United States Patent [19]

August et al.

[11] 4,222,983

[45] Sep. 16, 1980

[54] IMPRESSION COMPOSITIONS AND PROCESS FOR PREPARING IMPRESSIONS

[75] Inventors: Peter August, Seevetal; Wolfgang Hechtl, Burghausen; Richard Schmidlkofer, Mehring-Öd, all of Fed. Rep. of Germany

[73] Assignee: Wacker-Chemie GmbH, Munich, Fed. Rep. of Germany

[21] Appl. No.: 928,749

[22] Filed: Jul. 27, 1978

[30] Foreign Application Priority Data

Aug. 12, 1977 [DE] Fed. Rep. of Germany ....... 2736421

[51] Int. Cl.$^2$ ................................................ B29C 1/02
[52] U.S. Cl. ............................... 264/220; 260/37 SB; 264/222; 264/227; 433/228
[58] Field of Search ..................... 260/37 SB; 528/31; 32/17; 264/220, 222, 227

[56] References Cited

U.S. PATENT DOCUMENTS

| | | | |
|---|---|---|---|
| 3,082,527 | 3/1963 | Nitzsche et al. | 528/31 |
| 3,631,220 | 12/1971 | Wojdac | 260/37 SB |
| 3,844,992 | 10/1974 | Antonen | 260/37 SB |
| 3,948,848 | 4/1976 | Mink | 260/37 SB |
| 3,950,300 | 4/1976 | Hittmair et al. | 260/37 SB |
| 3,996,195 | 12/1976 | Sato et al. | 528/31 |

*Primary Examiner*—Lewis T. Jacobs

[57] ABSTRACT

Impression compositions containing (a) an organopolysiloxane having at least two alkenyl groups and containing at least 20 mol percent of monoorganosiloxane units, (b) an organopolysiloxane having at least 3 Si-bonded hydrogen atoms per molecule, (c) a catalyst which promotes the addition of Si-bonded hydrogen atoms to alkenyl groups and (d) 30 to 90 percent by weight of a filler, based on the total weight of the composition. Impressions are obtained by applying a composition containing components (a), (b), (c) and (d) to a surface of which an impression is to be made, crosslinking said composition and thereafter removing the formed structure from the contacted surface.

3 Claims, No Drawings

IMPRESSION COMPOSITIONS AND PROCESS FOR PREPARING IMPRESSIONS

The present invention relates to impression compositions and more particularly to a process for preparing impressions by crosslinking the impression compositions on the surface of which an impression is to be taken and thereafter removing the formed structure from the surface.

BACKGROUND OF THE INVENTION

Processes for preparing impressions of human and animal teeth have been described in German Patent Application No. 2,249,822. According to the process described in this German Patent Application, a composition containing (a) a diorganopolysiloxane having as terminal units triorganosiloxy groups each of which contains at least one vinyl group, i.e., an organopolysiloxane having at least two alkenyl groups per molecule, (b) an organopolysiloxane having at least 3 Si-bonded hydrogen atoms per molecule, (c) a catalyst which promotes the addition of Si-bonded hydrogen to alkenyl groups, and (d) up to 90 percent by weight of a filler, based on the total weight of the composition, is crosslinked while in contact with the surface of which an impression is to be taken, and thereafter the formed structure is removed from the surface of which the impression was taken.

When the process described in the German Patent Application is employed to obtain an impression simultaneously of more than one tooth, it was necessary to use a composition, such as an alginate, in order to obtain an impression whose inside diameter is greater than that of the final impression because the Shore-A hardness of the crosslinked products described in the German Patent Application is so low. Also, the use of a composition such as an alginate in making these impressions was very objectionable from a physiological point of view. From this first impression, it was necessary to prepare a positive from, for example gypsum and to use the positive to prepare a so-called impression spoon. Up to the present time, the material used for the impression spoon consisted of, for example, polyester or polymethyl acrylate. Then the impression spoon and a composition prepared in accordance with German Patent Application No. 2,249,822 were used to make the final impression. All of these steps are time consuming and expensive. Thus one of the advantages of this invention is that the compositions form impressions having a higher Shore-A hardness value and these compositions can be used for taking simultaneous impressions of more than one tooth even in the absence of an impression spoon and, generally, obtain impressions in the absence of stiffening agents or lining materials, i.e., materials which compensate for the difference in the dimensions of the somewhat larger impression and the actual dimensions of the tooth.

An added advantage of the process of this invention is when simultaneous impressions are taken of more than one tooth, there is no need to use an alginate, since the process of this invention makes it possible to obtain an impression whose inside dimensions are larger than those of the final impression and the first impression obtained from the process of this invention can be used to prepare a positive and an impression spoon from still another material with the aid of said positive, which itself can be used as an impression spoon. The impression spoon can accept the composition used in the preparation of the final impression; for example a composition of the type described in German Patent Application No. 2,249,822.

The latter application of the process of this invention has the added advantage that the impressions obtained from the crosslinked products prepared from the compositions of German Patent Application No. 2,249,822, adhere substantially better than the heretofore known impression spoons. This avoids the possibility that the final positives might be encumbered by errors which are caused by inadequate adhesion of the final impression on the impression spoon.

Therefore, it is an object of this invention to provide a composition which can be used to make impressions. Another object of this invention is to provide compositions for preparing impressions which have a higher Shore-A hardness. Still another object of this invention is to provide compositions for preparing impressions which have good storage stability. A further object of this invention is to provide a process for preparing impressions simultaneously of more than one tooth.

SUMMARY OF THE INVENTION

The foregoing objects and others which will become apparent from the following description are accomplished in accordance with this invention, generally speaking, by providing compositions for preparing impressions which comprises (a) an organopolysiloxane having at least two alkenyl groups and containing at least 20 mol percent of monoorganosiloxane units, (b) an organopolysiloxane having at least 3 Si-bonded hydrogen atoms per molecule, (c) a catalyst which promotes the addition of Si-bonded hydrogen atoms to alkenyl groups and (d) 30 to 90 percent by weight of a filler, based on the total weight of the composition. Also this invention relates to a process for preparing impressions which comprises crosslinking the composition while in contact with the surface of which an impression is to be taken and thereafter removing the formed structure from said surface.

DETAILED DESCRIPTION OF INVENTION

Siloxane units other than the monoorganosiloxane units which may be present in the organopolysiloxanes (a) used in the process of this invention are diorganosiloxane units, triorganosiloxane units and/or $SiO_{4/2}$ units. However, it is preferred that the proportion of diorganosiloxane units be at least 10 mol percent and the proportion of monoorganosiloxane units not exceed about 95 mol percent, and the $SiO_{4/2}$ units not exceed about 5 mol percent. Of course, the total mol percent present is equal to 100.

Monoorganosiloxane units can be represented by the formula $RSiO_{3/2}$, the diorganosiloxane units can be represented by the formula $R_2SiO$ and the triorganosiloxane units can be represented by the formula $R_3SiO_{\frac{1}{2}}$. In all of these formulas, R represents the same or different substituted and unsubstituted monovalent hydrocarbon radicals which should preferably contain from 1 to 12 carbon atoms.

Examples of hydrocarbon radicals represented by R are alkyl radicals, such as the methyl, ethyl, n-propyl, isopropyl, n-butyl and sec-butyl radical as well as octyl radicals and dodecyl radicals; cycloalkyl radicals such as the cyclopentyl, cyclohexyl and cycloheptyl radical; alkenyl radicals such as the vinyl and the allyl radical; aryl radicals such as the phenyl radical; alkaryl radicals such as tolyl radicals; and aralkyl radicals, such as the benzyl radical. Examples of substituted hydrocarbon radicals represented by R are preferably hydrocarbon radicals which are substituted with at least one fluorine atom, such as the 1,1,1-trifluoropropyl radical and the alpha,alpha, alpha-trifluorotolyl radical, and cyanoalkyl radicals, such as the beta-cyanoethyl radical. Because they are readily available, it is preferred that at least 50 percent of the R radicals be methyl radicals. However, since it is essential that the organopolysiloxanes (a) contain at least 2 alkenyl groups per molecule, not all R radicals may be methyl radicals.

Again, primarily because of their availability, it is preferred that the organopolysiloxanes (a) contain from 50 to 95 mol percent of units of the formula $(CH_3)_2SiO$ and 2 to 15 mol percent of units of the formula $CH_2\!=\!CH(CH_3)_2SiO_{\frac{1}{2}}$. Of course the sum of all the units is equal to 100 mol percent.

Although the organopolysiloxanes (a) may contain up to 5 percent by weight, it is preferred that the weight of Si-bonded hydroxyl groups and/or SiOR-groups, where R is the same as above, not exceed about 0.2 percent by weight.

It is preferred that the viscosity of the organopolysiloxanes (a) be in the range of from about 30,000 up to about 100,000 cSt at 25° C.

It is very surprising that organopolysiloxanes (a) having at least 20 mol percent of monoorganosiloxane units can be used in organopolysiloxane based compositions for the preparation of impressions because the crosslinkable organopolysiloxane compositions known heretofore, all contain at least 90 mol percent of diorganosiloxane units and thus a maximum of only 10 mol percent monoorganosiloxane units. This was due primarily to the fact that one skilled in the art would conclude that if the crosslinked product were to contain a greater percentage of monoorganosiloxane units, the product would no longer be sufficiently flexible to permit its removal from many types of structures of which impressions are taken. Another factor is that as the number of SiC-bonded organic radicals decreases, the adhesive properties of the siloxanes increases. This is illustrated by the fact that sodium silicate (waterglass) is sometimes used as an adhesive. Consequently, one skilled in the art would suspect that the cross-linked products containing at least 20 mol percent of monoorganosiloxane units would adhere to the surface and would be difficult to remove from the surface of which an impression is taken.

Any of the organopolysiloxanes containing at least 3 Si-bonded hydrogen atoms per molecule which have been used heretofore to crosslink organopolysiloxanes containing at least two alkenyl groups per molecule may be used as organopolysiloxanes (b) in the process of this invention. In general, these organopolysiloxanes contain from 0.01 to 1.7 percent by weight of Si-bonded hydrogen atoms. They may be cyclic, linear or branched and preferably consist of units of the formula;

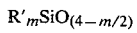

where R' represents hydrogen or has the same meaning as R and is preferably a methyl radical, with the proviso that at least 3 Si-bonded hydrogen atoms per molecule must be present and m represents 1, 2 or 3. Suitable examples of these compounds are those having $RHSiO\!-\!$, $R_2SiO\!-\!$ and $R_3SiO_{\frac{1}{2}}$ units with an Si-bonded hydrogen atom for each 3 to 100 silicon atoms and a viscosity of from 10 to 50,000 cP at 25° C.

The organopolysiloxane (b) which contains at least 3 Si-bonded hydrogen atoms per molecule is used in an amount sufficient to ensure that 0.75 to 15 and preferably 1.5 to 3 gram atoms of Si-bonded hydrogen are present for each gram molecule of alkenyl groups.

As catalysts (c) which promote the addition of Si-bonded hydrogen to alkenyl groups, it is possible to use for the purposes of this invention all catalysts which are capable of promoting the addition of Si-bonded hydrogen to alkenyl groups. Preference should be given to platinum catalysts such as finely dispersed platinum per se or platinum precipitated on carriers such as silicon dioxide, aluminum oxide, or activated carbon, platinum compounds and platinum complexes, for example platinum halides such as $PtCl_4$, $H_2PtCl_6.6H_2O$, $Na_2PtCl_4.nH_2O$, platinum-olefin complexes, for example ethylene, propylene or butadiene complexes, platinum-alcohol complexes, platinum-alcoholate complexes, platinum-ether complexes, platinum-aldehyde complexes, platinacetyl acetonate, reaction products of $H_2PtCl_6.6H_2O$ and monoketones, for example cyclohexanone, methylethyl ketone, acetone, methyl-n-propylketone, methylisobutylketone, diisobutylketone, acetophenone and mesityloxide, as well as platinum-vinylsiloxane complexes, such as platinum-divinyltetramethyldisiloxane complexes with or without any detectable amount of inorganic halogen.

Mixtures of various platinum catalysts, for example a mixture comprising a reaction product of $H_2PtCl_6.6H_2O$ with cyclohexanone and a platinum-divinyltetramethyldisiloxane complex which is free of detectable inorganic halogen may be used as well.

If a platinum catalyst is used as the catalyst (c) which promotes the addition of Si-bonded hydrogen to alkenyl groups, then it is preferred that quantities of from 0.5 to 500 ppm (parts by weight per million) and more preferably from 10 to 50 ppm be used, calculated on the basis of the platinum and based on the total weight of the composition.

If the process of this invention is used to obtain a dental impression in the oral cavity of a human being, the type and quantity of the catalyst which promotes the addition of Si-bonded hydrogen on alkenyl groups must of course be selected so that crosslinking of the composition in the mouth takes place within a maximum of 10 minutes so that the structure can be removed from the mouth without resulting in any change in the molded surface.

In order to obtain impressions having the least possible amount of shrinkage, the catalyst employed to promote the addition of Si-bonded hydrogen to alkenyl groups is preferably used in the absence of or substantially free of diluents having a boiling point below 100° C. at 760 mm Hg (abs.). Consequently it is best to use as a diluent, a portion of the organopolysiloxane (a) and/or another organopolysiloxane having alkenyl groups and/or the fillers and/or the non-volatile additives described herein below. If an organopolysiloxane other than organopolysiloxane (a) is used as a diluent for the catalyst, the diluent should not be employed in excess of about 15 percent by weight based on the weight of the organopolysiloxane (a).

The fillers used in the process of this invention may be reinforcing and/or non-reinforcing fillers. However, it is preferred that at least 65 percent by weight of the total fillers be non-reinforcing fillers. Examples of reinforcing fillers, i.e., fillers having a BET surface area of at least 50 m²/gm, are pyrogenically produced silicon dioxide, silicon dioxide aerogels, i.e., silicic acid hydrogels which have been dehydrated while maintaining their structure, and other types of precipitated silicon dioxide having a surface area of at least 50 m²/gm.

Examples of non-reinforcing fillers, i.e., fillers having a BET surface are less than 50 m²/gm are calcium carbonate, quartz meal, crystoballite meal, diatomite, talcum, aluminum silicate, zinc oxide and gypsum.

All of these fillers, especially the reinforcing fillers, may be pretreated with trimethylhalogensilanes, for example in accordance with German Patent Application No. 2,211,377, to provide fillers having organosilyl groups on their surface.

It is preferred that the fillers be employed in amounts of from 30 to 70 percent by weight, based on the total weight of the composition and more preferably in amounts which make the composition so highly viscous that it can be kneaded.

In addition to fillers, the compositions of this invention may contain additives which are generally used in compositions based on (a) organopolysiloxanes containing at least two alkenyl groups, (b) organopolysiloxanes having at least three Si-bonded hydrogen atoms per molecule, and (c) catalysts which promote the addition of Si-bonded hydrogen to alkenyl groups. Examples of such additives are pigments, soluble dyes, flavors and fragrances as well as compounds of the general formula:

$$CH_2=CHR_2SiO(SiR_2O)_nSiR_2CH=CH_2$$

where R is the same as above and n represents 0 or an integer having a value of from 1 to 6. Other compounds which may be included in the compositions of this invention are those of the formula:

$$R_2HSiO(SiR_2O)_pSiR_2CH=CH_2$$

where R is the same as above and p represents an integer whose value is such that the viscosity of these diorganopolysiloxanes is from 300 to 5000 cP at 25° C., as well as purely organic resins such as polyvinyl chloride powder.

When the compositions are to be stored for a period of time prior to their use, components (b) and (c) must be stored separately. In addition, when these compositions are to be stored for a period of time prior to use, it is preferred that pre-proportioned packaging, such as that described in German Patent Application No. 2,249,822 be used since such prepackaging avoids errors on the part of the end user as well as the time and effort required for mixing the appropriate amounts of ingredients.

Components (a) through (d) and such other additives as may be used, are normally mixed at room temperature and pressure, i.e., generally at temperatures between 10° and 30° C. and at approximately 760 mm Hg (abs.).

The process of this invention may be used in the preparation of impressions of human or animal teeth by placing the compositions of this invention in contact with the teeth of which impressions are to be obtained by conventional techniques known in the art. The compositions of this invention are then allowed to crosslink and the structure formed is then removed from the teeth. As previously described, precise impressions can thus be obtained without any need for an impression spoon prepared for said purpose. Nevertheless, as also mentioned heretofore, the process of this invention can be used for the preparation of impression spoons and the latter method is preferred. However the process of this invention may also be used for the preparation of other types of impressions, for example for the preparation of molds which are used for polyurethane foam reproductions.

In the following examples, all parts are by weight unless otherwise specified.

(i) The platinum-divinylmethyldisiloxane-complex and the diluent used in some of the following examples are prepared as follows:

To a mixture containing 10 parts of $H_2PtCl_6.6H_2O$, 20 parts of 1,3-divinyl-1,1,3,3-tetramethyldisiloxane and 50 parts of ethanol, are added 20 parts of sodium bicarbonate. With constant stirring, the mixture is heated to boiling under reflux, allowed to stand for 15 hours and then filtered. At approximately 12 mm Hg (abs) the volatile components are removed from the filtrate by distillation. The residue is dissolved in benzene. The solution is then filtered and the benzene is distilled off the filtrate. The residue is mixed by using as a diluent a vinyldimethylsiloxy terminated dimethylpolysiloxane having a viscosity of 1400 cP at 25° C. at a ratio such that the mixture contains 1 percent platinum, calculated as the element.

(ii) The platinum-cyclohexanone complex and diluent used in the other examples is prepared as follows:

A solution containing sufficient $H_2PtCl_6.6H_2O$ in 200 ml cyclohexanone, to ensure that the solution contains 0.5 percent by weight of platinum, calculated as the element, is heated for one hour at 100° C. and subsequently dried over anhydrous sodium sulfate.

EXAMPLE 1

Mixture A

About 149 parts of an organopolysiloxane consisting of 71.6 mol percent of units of the formula $CH_3SiO_{3/2}$, 20.6 mol percent of units of the formula $(CH_3)_2SiO$ and 7.8 mol percent of units of formula $CH_2=CH(CH_3)_2SiO_{\frac{1}{2}}$ and having a viscosity of 97,000 cP at 25° C. are mixed with 2.62 parts of the mixture containing 1 percent by weight of platinum which consists of a platinum-divinyltetramethyldisiloxane complex and the diluent whose preparation is described in (i) above, 1.64 parts of a 2 percent by weight solution of 1,3-divinyl-1,1,3,3-tetramethyldisiloxane, in the previously mentioned organosiloxane having monomethylsiloxane units, and 149 parts of quartz meal and 25 parts of a commercially available silicon dioxide, pyrogenically produced in the gaseous phase, and has a surface area of 200 m²/gm which had been hydrophobized to 60 percent by being treated with dimethyldichlorosilane.

Mixture B

About 121 parts of the organopolysiloxane having monomethylsiloxane units described above in the preparation of mixture A, are mixed with 50 parts of a trimethylsiloxy end-blocked polysiloxane having a viscosity of 80 cP at 25° C. which consists of 66.6 mol percent of methylhydrogensiloxane units and 33.4 mol percent of dimethylsiloxane units, 121 parts of quartz meal and 35 parts of the partially hydrophobized silicon dioxide described above in mixture A.

Mixtures A and B are kneaded together in a weight ratio of 1:1. The time which elapsed between combining mixture B with mixture A and the time crosslinking could be detected is approximately 60 seconds. The crosslinkable composition obtained is used to obtain an impression of part of the jaw in the mouth of a test subject. Approximately 8 minutes from the time mixture A is kneaded with mixture B, the non-sticking impression is removed from the mouth of the test subject. Immediately after removal, the impression has a Shore-A hardness of 85 to 88. Approximately 20 minutes later the impression has a Shore-A hardness of 92 to 93.

After storing mixtures A and B for about 6 months, the time which elapses between kneading together and detectable crosslinking and the time required for crosslinking in the mouth until a stable structure is obtained, is the same as the freshly prepared mixtures.

EXAMPLE 2

Mixture C

About 470 parts of an organopolysiloxane which consists of 71.6 mol percent of units of the formula $CH_3SiO_{3/2}$, 20.6 mol percent of units of the formula $(CH_3)_2SiO$ and 7.8 mol percent of units of the formula $CH_2=CH(CH_3)_2—SiO_{\frac{1}{2}}$, and having a viscosity of 45,000 cP at 25° C., are mixed with 6.3 parts of the platinum-divinyltetramethyldisiloxane-complex which contains 1 percent of platinum and the diluent whose preparation is described in (i) above, as well as 6.3 parts of a 10 percent by weight of a solution of 1,3-divinyl-1,1,3,3-tetramethyldisiloxane in the previously referred to organopolysiloxane having monomethylsiloxane units and having a viscosity of 45,000 cP at 25° C., 200 parts of quartz meal and 30 parts of the partially hydrophobized silicon dioxide described in mixture A.

Mixture D

About 427 parts of the organopolysiloxane having monomethylsiloxane units which was described in the preparation of mixture C, are mixed with 290 parts of a trimethylsiloxy end-blocked organopolysiloxane having a viscosity of 68.6 cP at 25° C. and which consists of 50 mol percent of methylhydrogensiloxane units and 50 mol percent of dimethylsiloxane units, 183 parts of quartz meal, 540 parts of talcum and 60 parts of the partially hydrophobized silicon dioxide described in mixture A.

Mixtures C and D are mixed with the aid of a spatula in a weight ratio of 2:3. Approximately 2 minutes elapsed from the time that mixture D is combined with mixture C and initial crosslinking is detected. The crosslinkable composition obtained is used to form an impression spoon in the mouth of a test person. Approximately 10 minutes after the composition has been inserted in the mouth, the non-sticking impression spoon is removed. Approximately 35 minutes from the time the impression spoon is removed from the mouth, it has a Shore-A hardness of 93.

Approximately 12 minutes from the time the impression spoon is removed from the mouth, a composition obtained pursuant to the example described in German Patent Application No. 2,249,822 adheres to the impression spoon.

EXAMPLE 3

Mixture E

About 80 parts of an organopolysiloxane consisting of 72.6 mol percent of units of the formula $CH_3SiO_{3/2}$, 20.9 mol percent of units of $(CH_3)_2SiO$ and 6.5 mol percent of units of $CH_2=CH(CH_3)_2SiO_{\frac{1}{2}}$ and having a viscosity of 324,000 cP at 25° C. are mixed with 1 part of the mixture containing the platinum-cyclohexanone complex described in (ii) above containing 0.5 percent of platinum and the diluent described heretofore, 0.5 part of a 10 percent by weight solution of 1,3-divinyl-1,1,3,3-tetramethyldisiloxane in the organopolysiloxane previously described having monomethylsiloxane units and a viscosity of 324,000 cP at 24° C., 35 parts of cristoballite meal, 60 parts of talcum and 10 parts of the hydrophobized silicon dioxide whose preparation is described in mixture A.

Mixture F

About 60 parts of the organopolysiloxane having monomethylsiloxane units which is described in the preparation of mixture E, are mixed with 30 parts of a trimethylsiloxy end-blocked organopolysiloxane consisting of 66.6 mol percent of methylhydrogensiloxane units and 33.4 mol percent of dimethylsiloxane units having a viscosity of 80 cP at 25° C., 25 parts of cristoballite meal, 50 parts of talcum and 20 parts of the partially hydrophobized silicon dioxide described in mixture A.

Mixtures E and F are kneaded together in a ratio of 1:1. Approximately 65 seconds elapsed from the time that mixture F is first kneaded with mixture E. The crosslinkable composition obtained is used to form an impression of a wooden statuette. After approximately 12 minutes, the non-sticking impression can be removed from the wooden statuette. About 25 minutes after the impression is removed, it has a Shore-A hardness of 93. After the impression has been stored for 8 days, linear shrinkage is only 0.04 percent.

In order to test the storage stability of these compositions, mixtures E and F are stored in closed containers for one week at 60° C. and then kneaded together in a weight ratio of 1:1. About 45 seconds elapsed from the time mixture F is first combined with mixture E and after approximately 14 minutes the impression can be removed from the wooden statuette without sticking. Approximately 30 minutes later the Shore-A hardness of the impression is 93. After the impression has been stored for 8 days, its linear shrinkage is only 0.05 percent. The properties of the composition and the shrinkage of the crosslinked structure obtained from said composition is essentially unaffected by heat aging.

In another test, mixtures E and F are kneaded in a ratio of 1:1 prior to storage. The crosslinked composition obtained is used to form an impression spoon in the mouth of a test person. The non-adhesive impression spoon is removed from the mouth of the test person after 10 minutes.

Twelve minutes after the impression spoon is removed the composition described in German Patent Application No. 2,249,822 is placed in the impression spoon and allowed to crosslink. The adhesion of the elastomer so obtained to the impression spoon is 1.2 $kp/cm^2$, while in a comparison test with an impression spoon made of polyethylene, the adhesion is 0.16 $kp/cm^2$ and on a third impression spoon made of stainless steel (V2A) it is 0.0 $kp/cm^2$, as measured in accordance with DIN (German Industrial Standard) 53273.

COMPARISON EXAMPLE

Mixture G

About 102.5 parts of a vinyldimethylsiloxy end-blocked dimethylpolysiloxane having a viscosity of 20,000 cP at 25° C. and 1.25 parts of the platinum-divinyltetramethyldisiloxane complex which contains 1 percent platinum and the diluent whose preparation was previously described, in (i) above, and 1.0 part of a 1 percent solution of 1,3-divinyl-1.1.3.3-tetramethyldisiloxane are mixed with the previously described dimethylpolysiloxane and 149 parts of quartz meal.

Mixture H

About 97.5 parts of the dimethylpolysiloxane which was described in the preparation of mixture G are mixed with 11 parts of a trimethylsiloxy end-blocked organopolysiloxane having a viscosity of 500 cP at 25° C. which consists of 90 mol percent of dimethylsiloxane units and 10 mol percent of methylhydrogensiloxane units and 145 parts of quartz meal.

Mixtures G and H are mixed together in a weight ratio of 1:1. The crosslinkable composition which corresponds to that obtainable in accordance with German Patent Application No. 2,249,822 results in an elastomer whose Shore-A hardness 24 hours after mixing of the two mixtures is only 58, not withstanding that the composition contains more filler than the compositions described in Examples 1 through 3.

What is claimed is:

1. A process for preparing impressions which comprises crosslinking a composition comprising (a) an organopolysiloxane containing at least 20 mol percent of monoorganosiloxane units and having at least two alkenyl groups per molecule, (b) an organopolysiloxane containing at least three Si-bonded hydrogen atoms per molecule, (c) a catalyst which promotes the addition of Si-bonded hydrogen to alkenyl groups and (d) 30 to 90 percent by weight of a filler, based on the total weight of the composition, while in contact with the surface of which an impression is to be taken, and thereafter removing the crosslinked structure from the surface.

2. The process of claim 1, wherein the organopolysiloxane (a) consists of from 50 to 90 mol percent of units of the formula $CH_3SiO_{3/2}$, 10 to 40 mol percent of units of the formula $(CH_3)_2SiO$ and 2 to 15 mol percent of units of the formula $CH_2=CH(CH_3)_2SiO_{\frac{1}{2}}$ in which the sum of all the units is equal to 100 percent.

3. Impression spoon prepared in accordance with the process of claims 1 or 2.

* * * * *